US009958438B2

(12) United States Patent
Sjolander

(10) Patent No.: US 9,958,438 B2
(45) Date of Patent: May 1, 2018

(54) MULTI-CHANNEL FLOWCELL

(71) Applicant: GE HEALTHCARE BIO-SCIENCES AB, Uppsala (SE)

(72) Inventor: Stefan Sjolander, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days. days.

(21) Appl. No.: 14/343,120

(22) PCT Filed: Sep. 28, 2012

(86) PCT No.: PCT/SE2012/051036
§ 371 (c)(1),
(2) Date: Mar. 6, 2014

(87) PCT Pub. No.: WO2013/055281
PCT Pub. Date: Apr. 18, 2013

(65) Prior Publication Data
US 2014/0219871 A1 Aug. 7, 2014

(30) Foreign Application Priority Data

Sep. 30, 2011 (SE) ...................... 1100724

(51) Int. Cl.
*G01N 33/53* (2006.01)
*G01N 21/05* (2006.01)
(Continued)

(52) U.S. Cl.
CPC ...... *G01N 33/5302* (2013.01); *B01L 3/50273* (2013.01); *B01L 3/502738* (2013.01);
(Continued)

(58) Field of Classification Search
CPC ......... G01N 33/54373; G01N 33/0031; G01N 21/553; G01N 21/554
(Continued)

(56) References Cited

U.S. PATENT DOCUMENTS 5,164,589 A 11/1992 Sjodin
5,313,264 A * 5/1994 Ivarsson et al. ................ 356/73
(Continued)

FOREIGN PATENT DOCUMENTS

EP 1345841 9/2003
WO 2005046859 6/2005
(Continued)

OTHER PUBLICATIONS

PCT/SE2012/051036 ISRWO Dated Jan. 9, 2013.
(Continued)

*Primary Examiner* — Dennis White
*Assistant Examiner* — Bryan Kilpatrick
(74) *Attorney, Agent, or Firm* — Rong Zhang

(57) ABSTRACT

A flow cell unit to be docked against a flat lid surface to form a closed flow cell arrangement, the flow cell unit comprising a top surface with protruding walls of elastic material defining three or more adjacent elongated flow channels, each flow channel comprises a first fluid port and a second fluid port, wherein the walls separating adjacent flow channels comprises a valve section of reduced height, thereby allowing selective opening and closing of a flow path transverse to the elongated flow channels by controlling the docking force between flow cell and the lid surface to an open docking state and a closed docking state respectively.

11 Claims, 17 Drawing Sheets

(51) Int. Cl.
  *B01L 3/00* (2006.01)
  *G01N 21/03* (2006.01)
  *G01N 33/543* (2006.01)
  *G01N 21/552* (2014.01)
  *G01N 33/00* (2006.01)

(52) U.S. Cl.
  CPC ........... *G01N 21/05* (2013.01); *G01N 21/553* (2013.01); *G01N 33/54366* (2013.01); *B01L 2200/0636* (2013.01); *B01L 2300/044* (2013.01); *B01L 2300/0877* (2013.01); *B01L 2300/123* (2013.01); *B01L 2400/0481* (2013.01); *G01N 21/554* (2013.01); *G01N 33/0031* (2013.01); *G01N 33/54373* (2013.01); *G01N 2021/0346* (2013.01)

(58) Field of Classification Search
  USPC ..... 422/69, 82.05, 82.11, 501, 502; 436/164
  See application file for complete search history.

(56) References Cited

U.S. PATENT DOCUMENTS

| | | | |
|---|---|---|---|
| 5,376,252 | A | 12/1994 | Ekstrom et al. |
| 6,192,168 | B1 | 2/2001 | Feldstein et al. |
| 7,105,356 | B2 | 9/2006 | Malmqvist et al. |
| 7,314,718 | B1 | 1/2008 | Dasgupta et al. |
| 8,105,845 | B2 | 1/2012 | Notcovich et al. |
| 2001/0035947 | A1 | 11/2001 | Fry et al. |
| 2003/0186426 | A1 | 10/2003 | Brewer et al. |
| 2004/0253821 | A1 | 12/2004 | Howitz et al. |
| 2006/0245978 | A1 | 2/2006 | Prins |
| 2008/0108122 | A1 | 5/2008 | Paul et al. |
| 2008/0219888 | A1 | 9/2008 | Lawson et al. |
| 2008/0317627 | A1 | 12/2008 | Shirai et al. |
| 2010/0061892 | A1 | 3/2010 | Flaim et al. |
| 2010/0238443 | A1 | 9/2010 | Claypool et al. |

FOREIGN PATENT DOCUMENTS

| | | |
|---|---|---|
| WO | 2007033385 | 3/2007 |
| WO | 2008052358 | 5/2008 |
| WO | 2008127269 | 10/2008 |
| WO | 2011078777 | 6/2011 |

OTHER PUBLICATIONS

European Patent Office Supplementary Search Report for EP Application No./Patent No. 12839366.7-1554 / 2761295 dated Apr. 13, 2015 (3 pages).

JP Office Action dated Jul. 6, 2016 for JP Application No. 2014-533245 (3 pages).

\* cited by examiner

MULTI-CHANNEL FLOWCELL

This application is a filing under 35 U.S.C. 371 of international application number PCT/SE2012/051036, filed Sep. 28, 2012, which claims priority to Sweden application number 1100724-2 filed Sep. 30, 2011, the entire disclosure of which is hereby incorporated by reference.

FIELD OF THE INVENTION

The present invention relates to a flow cell unit, and a fluidic system for biosensor system or the like, and more particularly to a flow cell unit, and a fluidic system for a biosensor system with increased capacity.

BACKGROUND OF THE INVENTION

Biosensor systems that can monitor interactions between molecules, such as biomolecules, in real time are maintaining increasing interest. A representative such biosensor system is the BIACORE® Surface Plasmon Resonance (SPR) instrumentation sold by GE Healthcare which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a "sensorgram".

SUMMARY OF THE INVENTION

The object of the invention is to provide a new flow cell unit, and a fluidic system using the same, which flow cell unit, and fluidic system overcomes one or more drawbacks of the prior art flow cell units, and a fluidic systems. This is achieved by the flow cell unit, and a fluidic system as defined in the independent claims.

One advantage with the flow cell arrangement of the present invention is that it allows increased number of detector spots for interaction studies in a robust, simple, low-cost, and efficient way. Furthermore embodiments of the flow cell arrangement allow faster provision of two-dimensional detection spot arrays.

A more complete understanding of the present invention, as well as further features and advantages thereof, will be obtained by reference to the following detailed description and drawings.

DETAILED DESCRIPTION OF THE INVENTION

Figure 1:
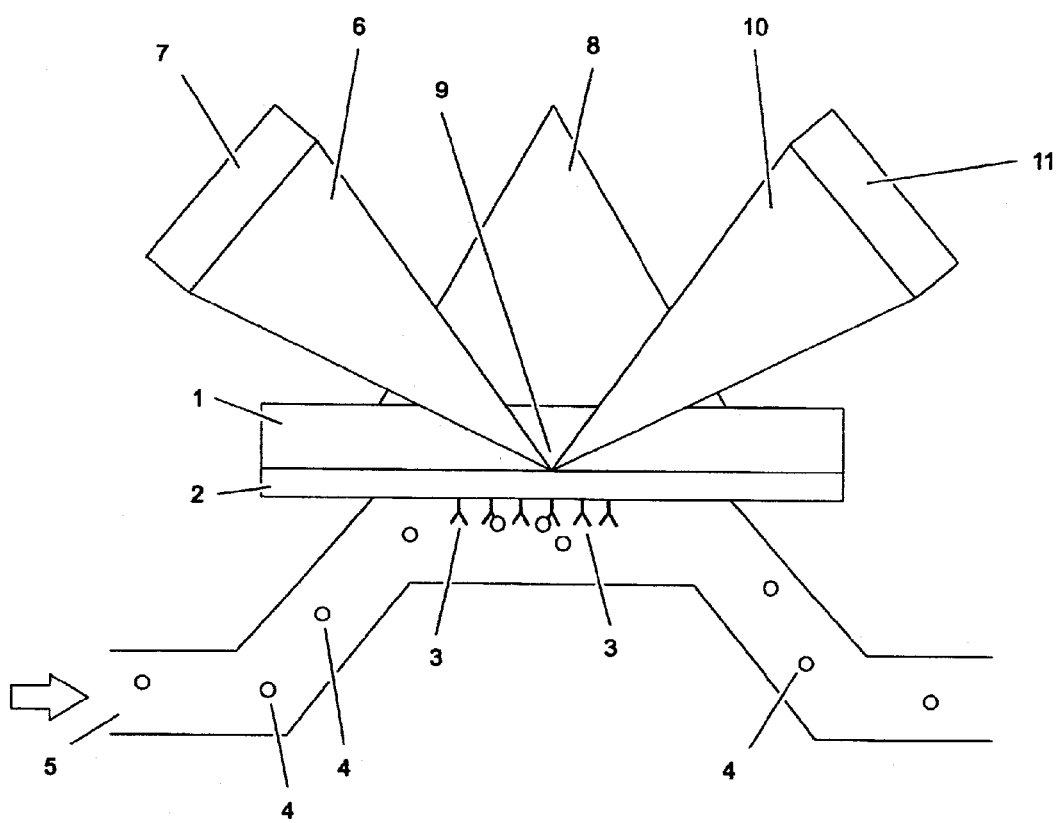
FIG. 1 is a schematic side view of a biosensor system based on SPR.

As mentioned above, the present invention relates to

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

Before describing the present invention in more detail, however, the general context in which the invention is intended to be used will be described.

Chemical sensors or biosensors are typically based on label-free techniques, detecting a change in a property of a sensor surface, such as e.g. mass, refractive index, or thickness for the immobilised layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by GE Healthcare, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized within the sensing volume (detection volume) at the surface, whereas "analyte" includes any specific binding partner thereto.

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip which is contacted with the sample by a microfluidic flow system. The metal film is a thin layer of gold on the chip surface. SPR causes a reduction in the intensity of the reflected light at a specific angle range of reflection. The angle of minimum reflected light intensity, so-called SPR-angle, varies with the refractive index close to the metal surface on the side opposite from the reflected light, in the BIACORE® system the sample side.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Mainly monochromatic p-polarised light 6 from an illumination unit 7 (e.g. LED) is coupled by a prism 8 to the glass/metal interface 9 where the light undergoes attenuated total reflection due to the SPR, forming the SPR-curve. The intensity of the reflected light beam 10 is detected by an optical detection unit 11 (e.g. a photodetector array).

When molecules in the sample bind to the capturing molecules on the sensor chip surface, the concentration, and therefore the refractive index at the surface changes and an SPR response, change in SPR-angle, intensity, or SPR-curve shape parameter, due to the shift in SPR-curve angular position, is detected. Plotting the response against time during the course of an interaction will provide a quantitative measure of the progress of the interaction. Such a plot, or kinetic or binding curve (binding isotherm), is usually called a sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, or SPR-curve centroid angle, which for most proteins and other biomolecules correspond to a change in concentration of about 1 pg/mm$^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when the sample flow is replaced by, for example, a buffer flow. This step is indicated on the sensorgram by a drop in RU over time as analyte dissociates from the surface-bound ligand.

Figure 2:
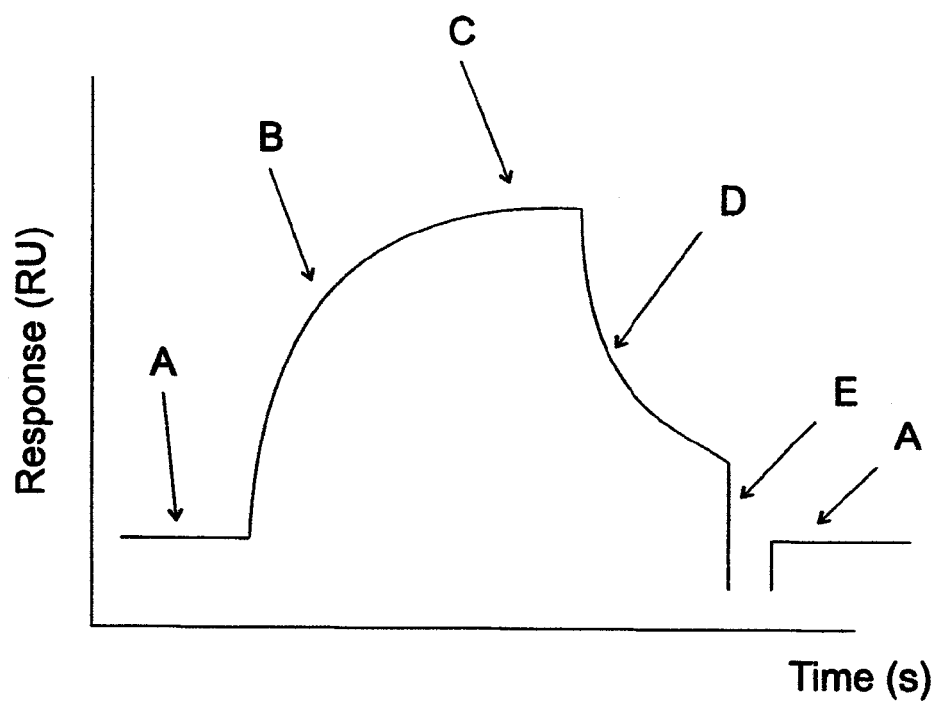
FIG. 2 is a representative sensorgram where the binding curve has visible association and dissociation phases.

A representative sensorgram (binding curve) for a reversible interaction at the sensor chip surface is presented in FIG. 2, the sensing surface having an immobilised capturing molecule, or ligand, for example an antibody, interacting with a binding partner therefor, or analyte, in a sample. The vertical axis (y-axis) indicates the response (here in resonance units, RU) and the horizontal axis (x-axis) indicates the time (here in seconds). Initially, buffer is passed over the sensing surface giving the baseline response A in the sensorgram. During sample injection, an increase in signal is observed due to binding of the analyte. This part B of the binding curve is usually referred to as the "association phase". Eventually, a steady state condition is reached at or near the end of the association phase where the resonance signal plateaus at C (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of sample injection, the sample is replaced with a continuous flow of buffer and a decrease in signal reflects the dissociation, or release, of analyte from the surface. This part D of the binding curve is usually referred to as the "dissociation phase". The analysis is ended by a regeneration step where a solution capable of removing bound analyte from the surface, while (ideally) maintaining the activity of the ligand, is injected over the sensor surface. This is indicated in part E of the sensorgram. Injection of buffer restores the baseline A and the surface is now ready for a new analysis.

From the profiles of the association and dissociation phases B and D, respectively, information regarding the binding and dissociation kinetics is obtained, and the height of the resonance signal at C represents affinity (the response resulting from an interaction being related to the change in mass concentration on the surface). This will now be explained in more detail below.

A detailed discussion of the technical aspects and the basic optical principles of BIACORE® instruments and the phenomenon of SPR may be found in U.S. Pat. No. 5,313,264.

Figure 3A:
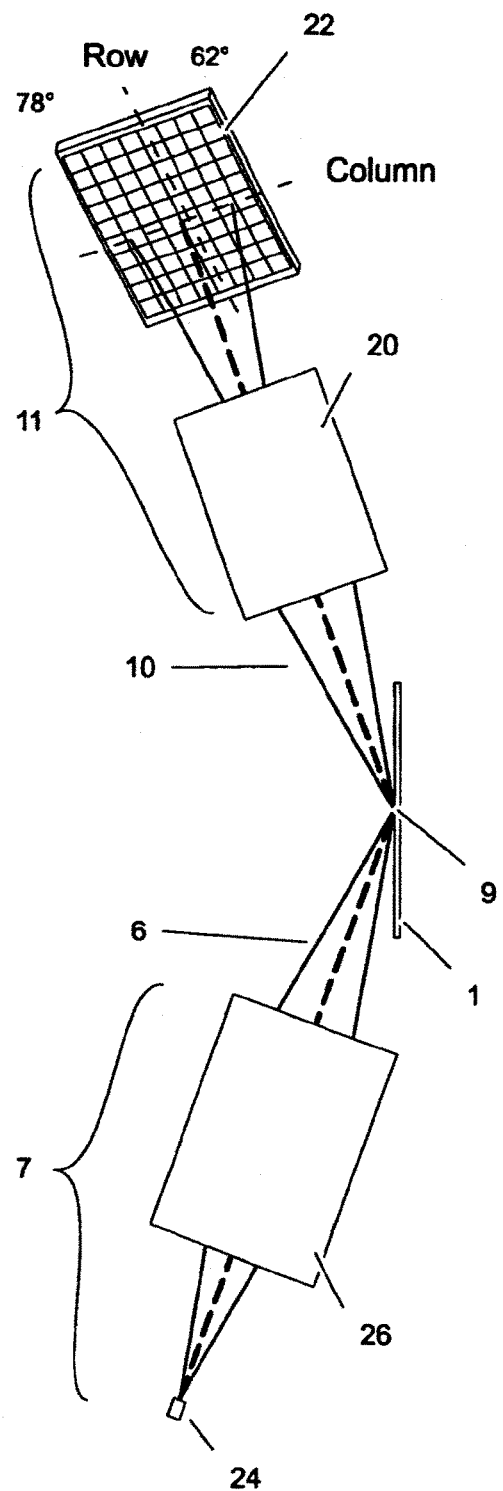
FIGS. 3a and 3b show a schematic view of a prior art SPR biosensor system.
Figure 3B:
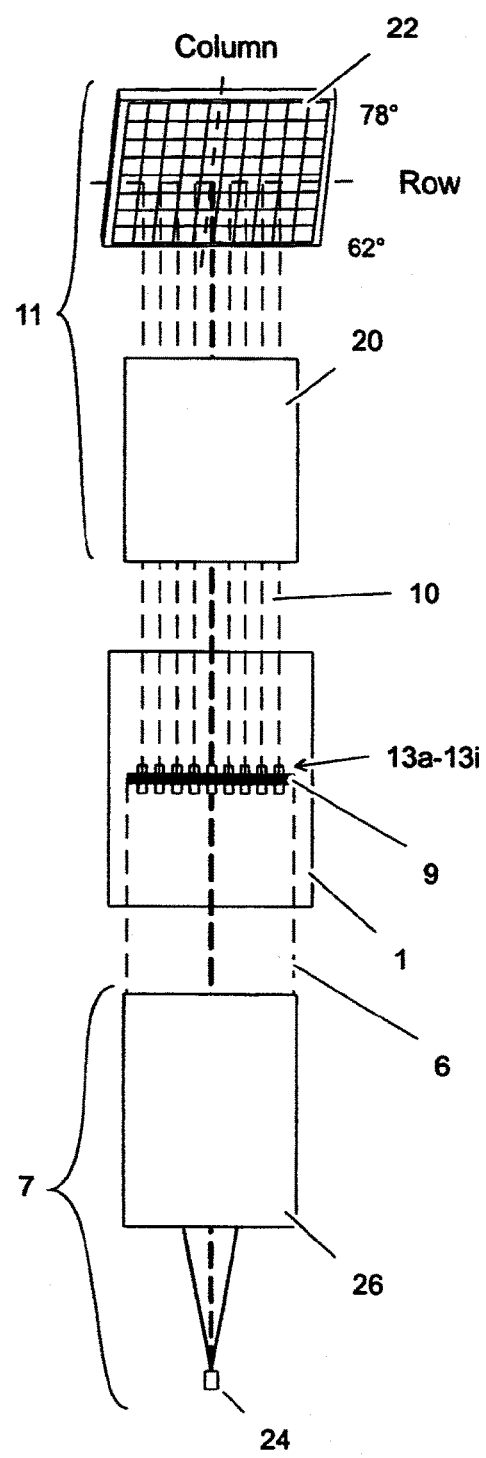
Figure 4A:
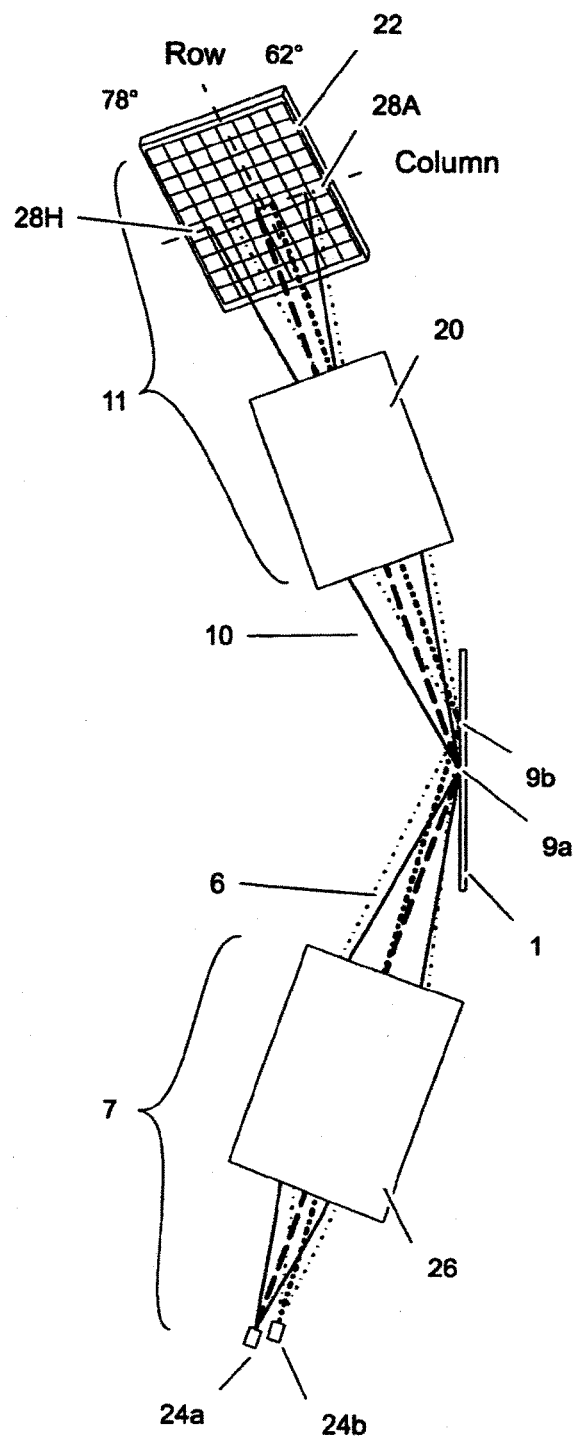
FIGS. 4a and 4b show a schematic view of one embodiment of a two-line SPR biosensor system.
Figure 4B:
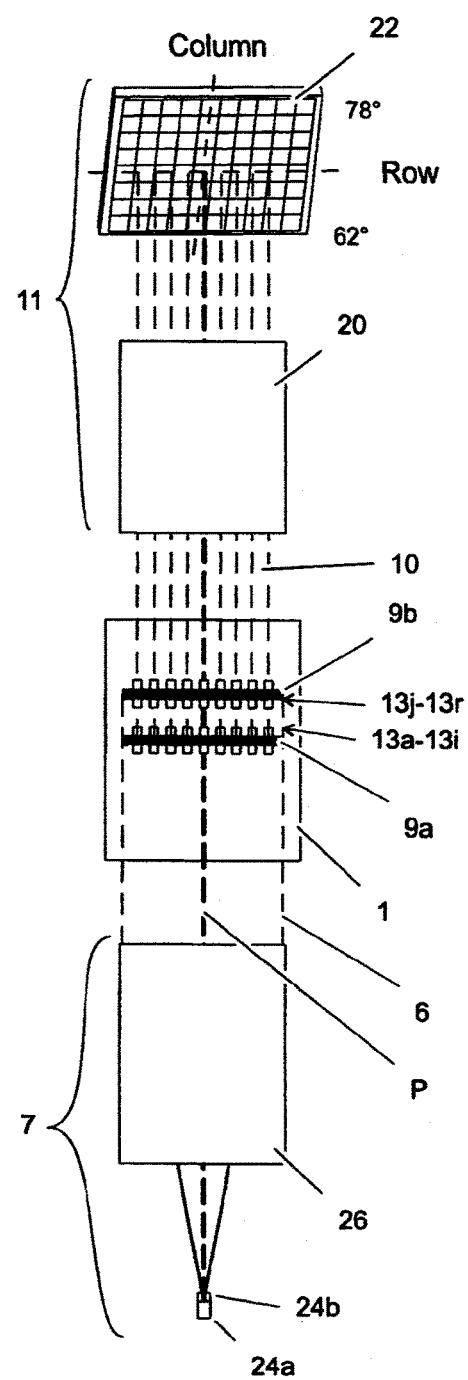
Figures 5A, 5B:
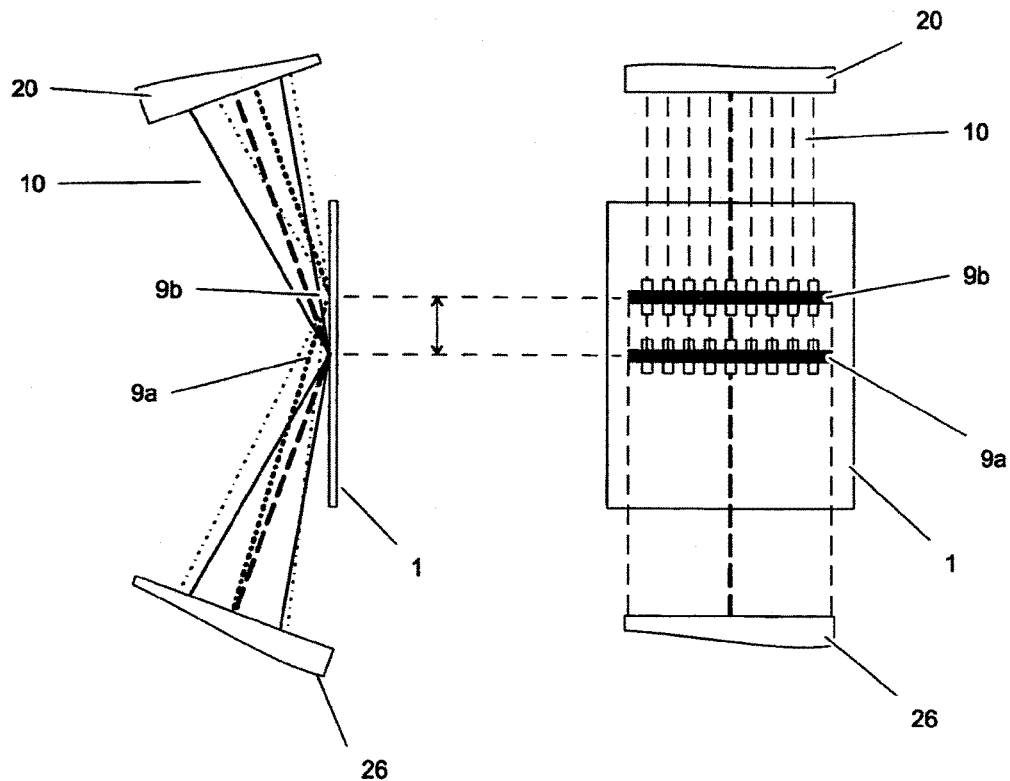
FIGS. 5a and 5b show enlarged sections of the SPR biosensor system of FIGS. 4a and 4b.

FIGS. 3a and 3b schematically illustrate the optical system in such a prior art BIACORE® system, where FIG. 3b is a top view and FIG. 3a is a cross-sectional side view of the plane P in FIG. 3b. Such systems comprises an illumination unit 7 comprising a light source 24 and wedge forming optics 26, arranged to direct a wedge shaped beam of light 6 at a line shaped detection area 9 on the SPR sensor surface 2 transverse to the direction of propagation of light. For illustrative purposes, all refractive elements in the light path have been omitted (e.g. optics for coupling the beam to the sensor surface like a prism as is shown in FIG. 1) or replaced by general "optics" units (e.g. 20 and 26). The wedge shaped beam of light 6 is essentially uniform in the transverse direction as illustrated in FIG. 3b, and strikes the illustrated line shaped detection area 9 at angles of incidence relevant for SPR detection such as from 62 to 78 degrees. Rays with all the intermediate (e.g. between 62° and 78 degree) angles of incidence are present in the beam. The system further comprises a detection unit 11 with special, anamorphic detection optics 20 for directing light reflected from the SPR sensor surface 1 onto a two-dimensional optical detector unit 22 such that the angle of reflection is imaged along one dimension (column) and the width of the detection area along the other (row). For illustration purposes, consider only one incident plane, light incident e.g. at 62° is reflected on the sensitized surface 9 and is imaged by the detection optics 20 on only one single detection element 28A of the two-dimensional optical detector unit 22. Similarly, light incident with an angle of 78° will be imaged on one single single detection element 28H. Light having incident angle values intermediate between 62 and 78 degrees will similarly strike those single detection elements which are situated between elements 28A and 28H in the same detector column; in FIGS. 3a and 3b this is illustrated as being a vertical column.

The light source 24, e.g. a light emitting diode, emits a type of light that is substantially monochromatic in character (bandwidth ~50 nm), and furthermore is incoherent and has a center wavelength of an order of magnitude of about 650 to about 850 nm. Alternatively, the light source 24 is a laser, e.g. a semiconductor laser, a dye laser or a gas laser, emitting substantially monochromatic and coherent light. The light source 24 may also take the form of a low coherent edge emitting diode like either a superluminescent or superradiant diode (SLD), or an ELED.

Light rays having a different plane of incidence parallel to the plane of incidence P will in a similar way be imaged on individual detection elements belonging to other columns of the two-dimensional optical detector unit 22. Every detection element of a row thus corresponds to one specific angle of incidence. Thus to each column of the two-dimensional optical detector unit 22 corresponds a respective part of the sensing surface as seen in the transverse direction of the conduit portion. Depending on the width of the sample flow channel, the magnification of the detection optics, the surface dimensions of the individual detection elements, and the spaces between them, a particular number of detection element columns may be required for imaging the total width of the flow channel portion in question.

In the embodiment of FIGS. 3a and 3b, nine detection spots 13a-13i for interaction analysis are illustrated allowing registration of up to nine independent interactions simultaneously. As is well established in the art, a ligand is immobilized on each detection spot (one or more spots may intentionally be left without ligand to serve as a reference channel for mitigating non-specific contributions to the SPR response) and the same or different analytes are brought into contact with the sensor spots. According to one embodiment, as is shown in U.S. Pat. No. 5,313,264, each detection spot 13 is associated with a flow channel for passing the analyte over the spot, but alternatively two or more detection spots 13 may be arranged in one single flow cell e.g. capable of hydrodynamic addressing of individual detection spots 13 (as is disclosed in U.S. Pat. No. 7,811,515).

In the prior art systems of the type shown in FIGS. 3a and 3b, the max theoretical number of detection spots is limited by the number of pixel rows on the two-dimensional optical detector unit 22, while the practical number depends on the size of the detection spots 13 and associated fluidic system. However, in many situations there is a need for higher throughput and thus more detection spots are desired on the sensor surface.

FIGS. 4a to 5b shows a schematic embodiment of a new Surface Plasmon Resonance (SPR) biosensor system concept, wherein the number of detection spots 13 is doubled without the need to significantly redesign the optics of the system. This system concept is disclosed in great detail in the co-pending patent application SE1150890-0

By providing a second light source 24b spaced apart from the first light source 24a by a suitable distance in the plane P, and suitably controlling the emission of light from the light sources, the illumination unit is arranged to selectively direct the wedge shaped beam of light 6 at two spaced apart line shaped detection areas 9a and 9b, respectively, on the SPR sensor surface 1 transverse to the direction of propagation of light. In general, all elements of the prior art SPR system of FIGS. 3a and 3b may be left unchanged, but as will be appreciated by a person skilled in the art there may be optimizations available. It shall be noted that the displacement of the second light source 24b and the associated beam paths is exaggerated for illustrative purposes, and the real displacement in a working optical design may be very small to achieve a suitable distance between the detection areas 9a and 9b on the sensor surface. The real displacement may further be restricted by the optical properties (e.g. aperture/imaging area) of all other optical components along the path.

According to one embodiment containing two light sources 24a and 24b about 0.3 mm apart, two light beams could be generated at the same time giving two detection areas 9a and 9b about 1 mm apart on the sensor surface 1.

Since the two detection areas 9a and 9b for each detection spot 13 pair (spots arranged in the same plane parallel to the plane P) will be imaged onto the same pixel column on the two-dimensional optical detector unit 22 the two interaction responses measured as one SPR-curve (one dip in the reflectance curve) at the time, cannot be registered completely simultaneous. Therefore, in order to register interaction data independently from detection spots 13 along the two detection areas 9a and 9b, the two light sources 24a and 24b are alternately switched on and off at a suitable frequency, in synchronization with the readout from the two-dimensional optical detector unit 22. By this, two nearly simultaneous sets of sensorgrams can be generated, one for each of the two detection spot-rows.

Figures 6A, 6B:
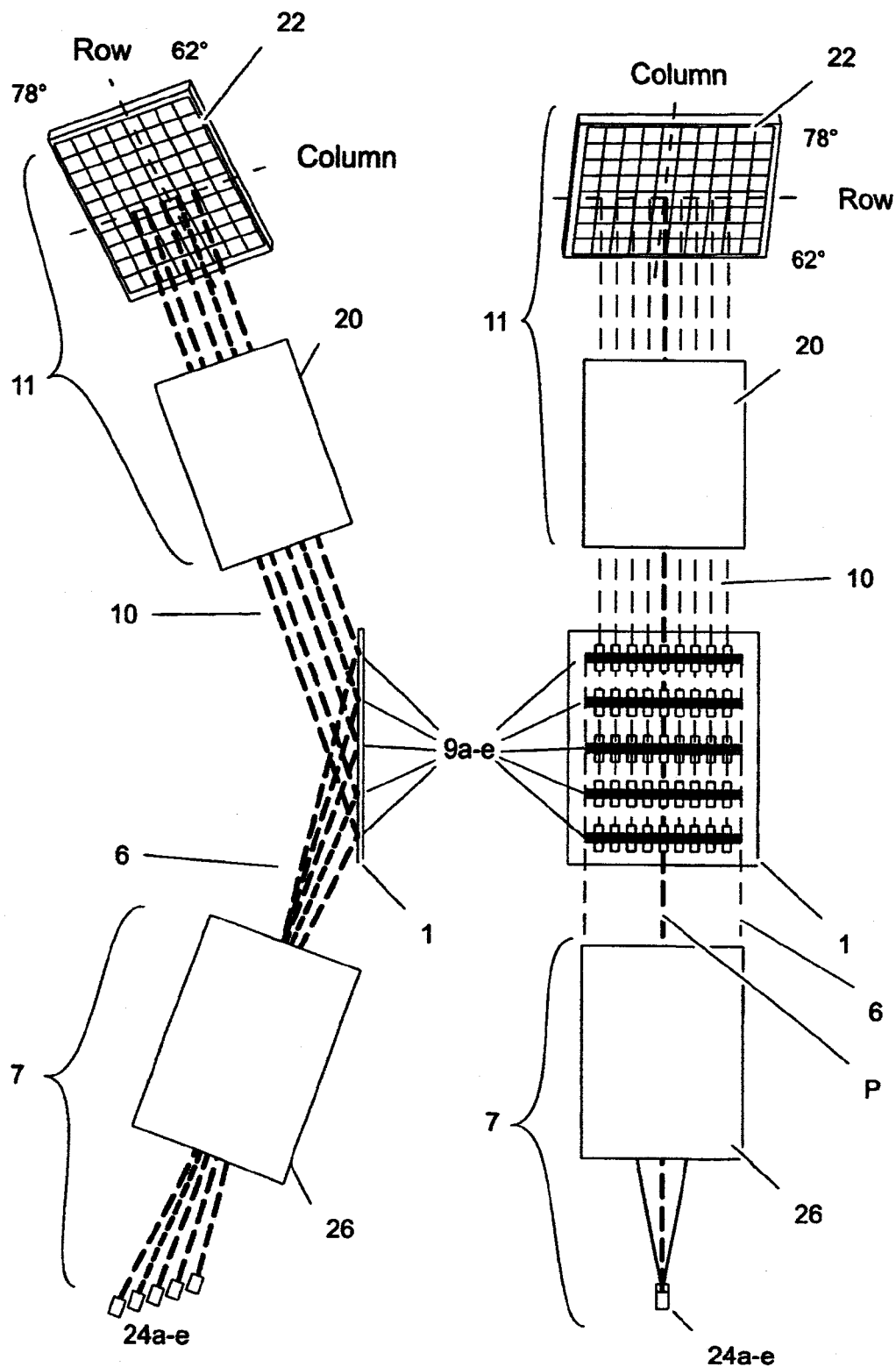
FIGS. 6a and 6b show a schematic view of one embodiment of a 5-line SPR biosensor system.
Figure 7A:
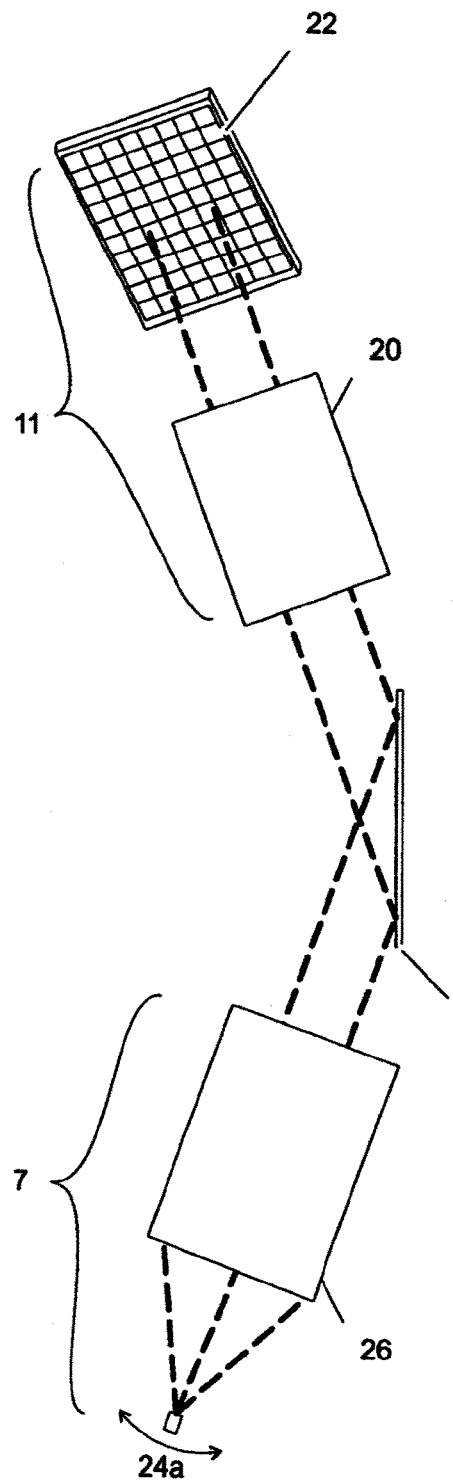
FIGS. 7a and 7b show a schematic view of one embodiment of a two-dimensional SPR biosensor system.
Figure 7B:
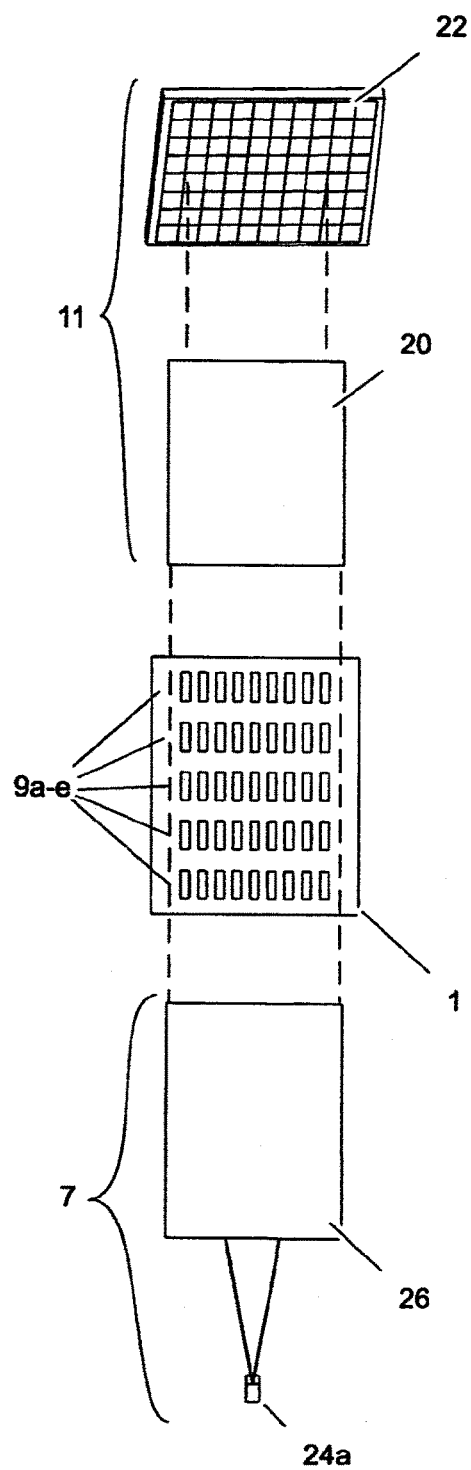

As previously mentioned, the design does not need to be limited to two detection areas 9a and 9b, and FIGS. 6a and 6b discloses an embodiment with 5 parallel detection areas 9a to 9e, hence providing 45 detection spots 13.

Further, another way to increase the number of detection spots significantly is to use a true two-dimensional SPR detection system where the whole sensor surface is imaged onto a two-dimensional optical detector unit 22 while scanning the incident angle of the light, one embodiment of such a system is schematically disclosed in FIGS. 6a and 6b wherein the number of detection spots 13 is the same as in the embodiment of FIGS. 6a and 6b. Further details of a 2D SPR system can e.g. be found in US2009-0213382.

However, in order to fully gain the benefits of increased optical detection capacity, there is a need for flow cell arrangements capable of providing liquid handling to provide the corresponding number of individual detection spots in an efficient way.

Figures 8A, 8B:
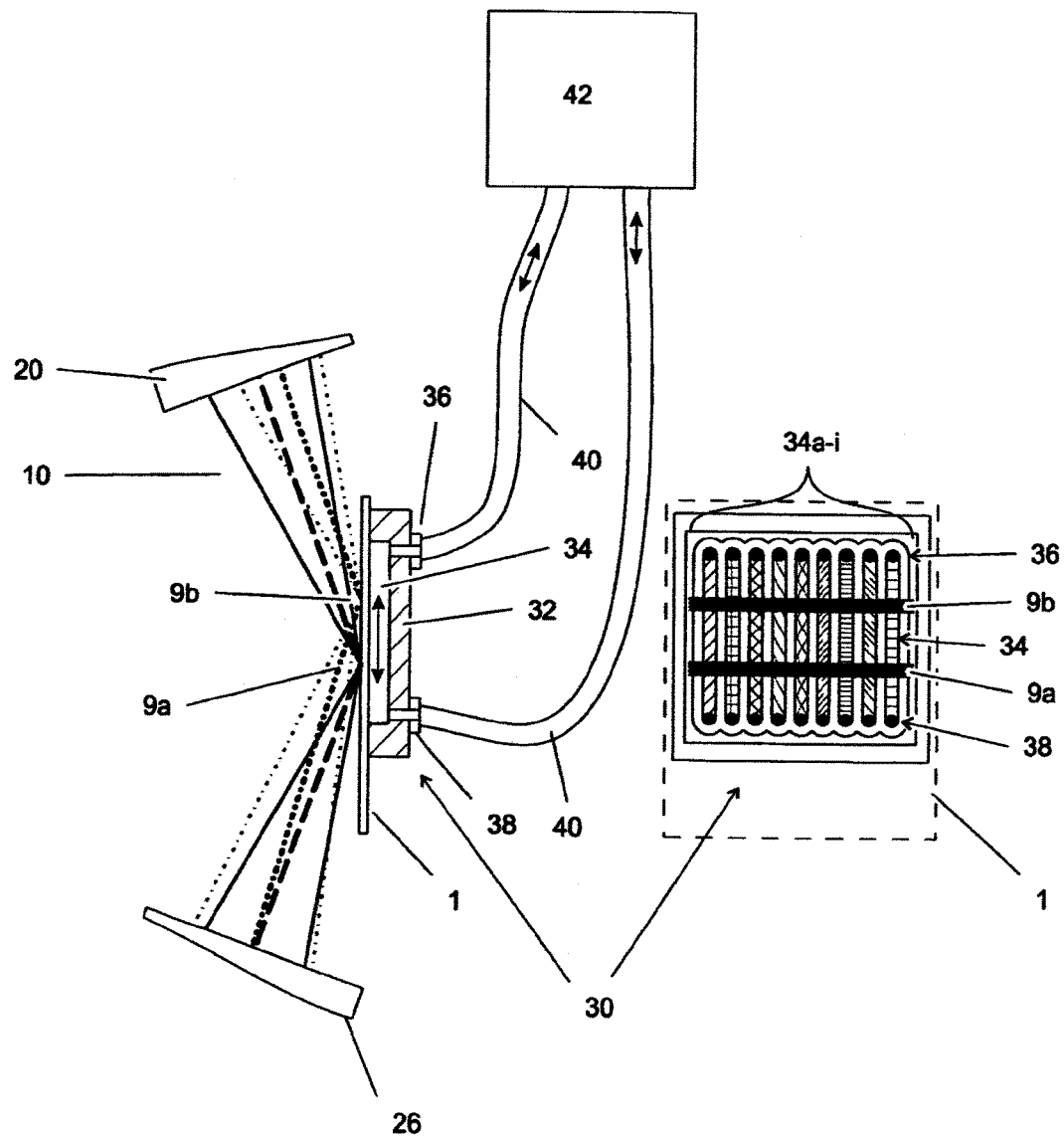
FIGS. 8a and 8b show a flow cell arrangement according to one embodiment.

FIGS. 8a and 8b schematically disclose a flow cell arrangement 30 comprising a flow cell unit 32 to be docked against the sensor surface 1 by applying a docking force to form separate elongated flow channels 34a-i transverse to the two detection areas 9a and 9b. Each flow channel 34a-i comprises a first fluid port 36 and a second fluid port 38 to enable a fluid flow in the flow channel 34. As will be evident below, both first and second fluid ports 36, 38 may be used as inlet and/or outlet ports in order to provide the desired flow patterns in the flow cell arrangement 30.

In the disclosed embodiments, the flow cell unit 32 is shown docked to a sensor surface of a SPR biosensor element, but in a general fluidic system, the flow cell unit 32 may e.g. be docked against any suitable flat lid surface capable of forming a closed flow cell arrangement together with the flow cell unit 32.

The fluid flow through the flow cell arrangement is controlled by a fluid control system 42 connected to the first and second fluid ports 36, 38 of the flow cell unit 30 by fluid conduits 40. In the disclosed embodiment, the fluid conduits 40 are only shown connected to the ports 36, 38 of one single fluid channel 34, but it should be understood that all ports 36, 38 of all fluid channels 34a-i are connected to the fluid control system 42 by corresponding conduits 40. Moreover, the conduits 40 are shown e.g. as tubes or capillaries, but according to an alternative embodiment, the conduits may be formed in an integral fluid block. The fluid control system 42 may be any suitable system capable of controlling the flow in the flow cell arrangement in accordance with the specific requirements of the fluidic system wherein the flow cell arrangement is used. According to one embodiment, the fluid control system 42 comprises one dedicated pump (not shown) for each fluid channel 34 and associated valves (not shown) in order to independently control the fluid flow in each fluid channel 34. Alternatively, the fluid control system 42 comprises a multi-channel pump to control the fluid flow simultaneously in two or more of the flow channels, e.g. a multi-channel peristaltic pump or the like.

In order to provide the desired two dimensional structure of detection spots, the flow cell arrangement according to the present invention is arranged to allow an alternative flow pattern transverse to the elongated fluid channels 34a-I, as is disclosed in more detail with reference to FIGS. 9a-15d. According to one embodiment, the whole sensor surface 1 may be addressable to define detection spots 13 and the detection spots are defined by a fluidic process in alignment with the optical detection system or the like whereby the resulting detection spots in general are defined by intersections between fluid channels and the transverse flow pattern. Alternatively the sensor surface 1 comprises discrete sensor surfaces arranged in an array that is aligned with and which may be addressable by the flow cell arrangement.

Figure 9A:
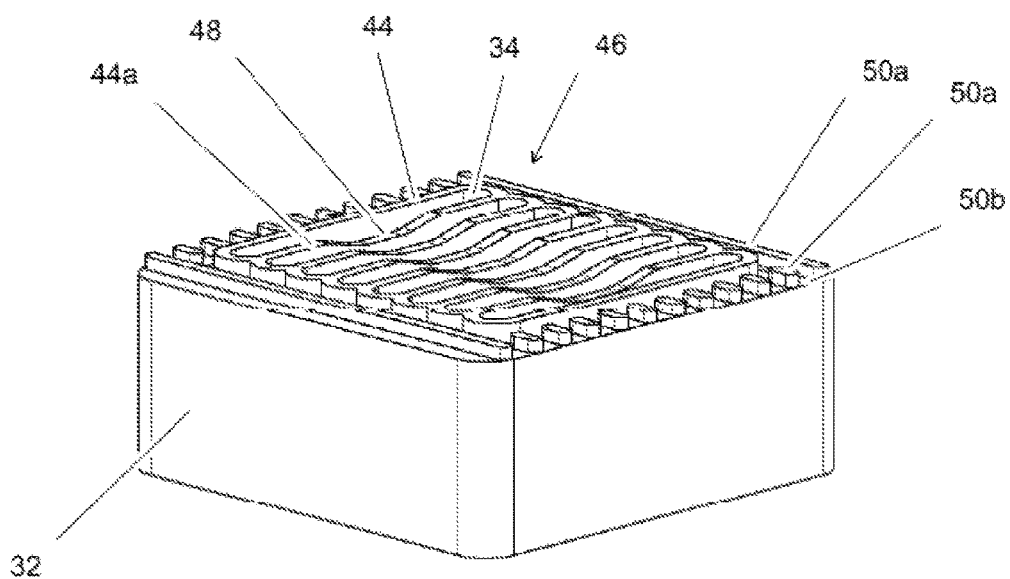
FIGS. 9a and 9b show a flow cell unit according to one embodiment.
Figure 9B:
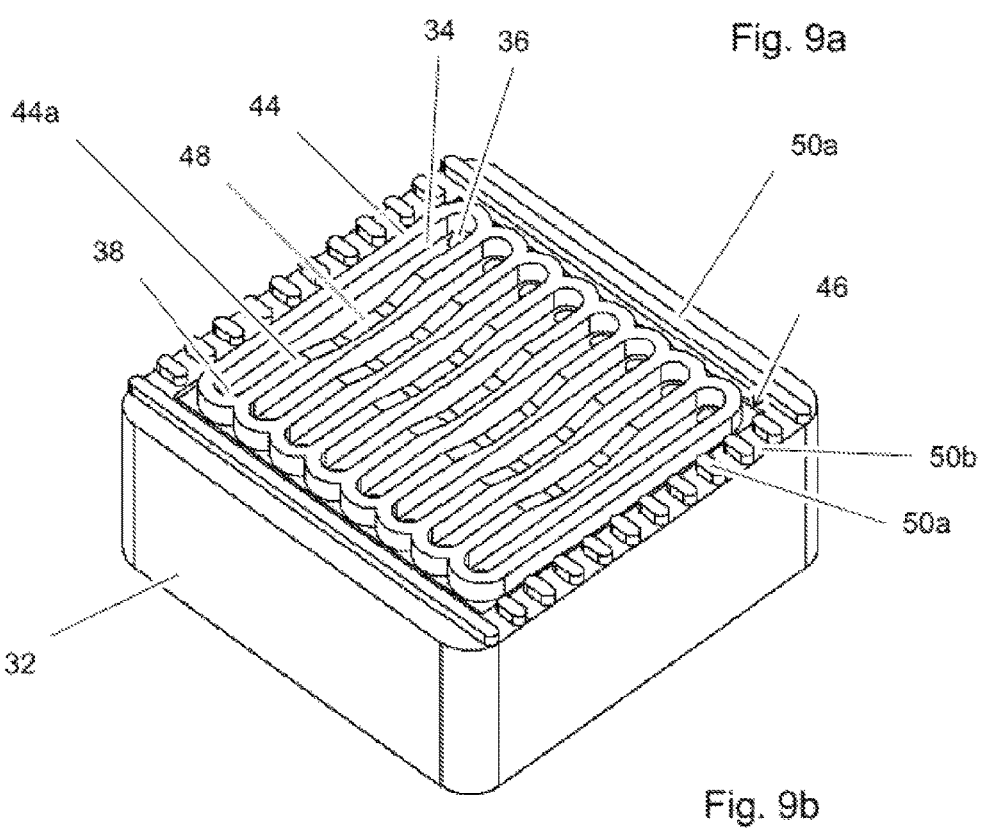

FIGS. 9a and 9b show, in two perspective views, one embodiment of a flow cell unit 32 according to the present invention with 8 adjacent elongated flow channels 34a-h defined by walls of elastic material 44 protruding a top surface 46 of the flow cell unit 32. The walls 44b separating adjacent flow channels 34 comprises a valve section 48 of reduced height, thereby allowing selective opening and closing of a flow path transverse to the elongated flow channels 34 by controlling the docking force between flow cell unit 32 and the SPR sensor surface 1 to an open docking state and a closed docking state respectively (which is schematically shown in FIGS. 10b-d). In order to achieve the selective open and closed docking states, the walls 44 should be made of a suitable elastic material that can be deformed in order to encompass the valve functionality, while having suitable chemical stability with respect to the fluids to be used in the system. According to one embodiment the walls are made of an elastomer such as silicone rubber (PDMA, PDMS) or the like. The whole flow cell unit 32 may e.g. be molded in a suitable elastic material, but alternatively, sections of the flow cell unit 32 may be formed in another material, such as a rigid material providing increased support during docking, and whereby the elastic walls 44 attached to the top surface 46 of the flow cell unit 32 by suitable means, such as co-molding or the like. As is shown in FIGS. 9a and 9b, the valve sections 48 are formed with a flat valve face 48a and inclined segments 48b extending from the valve face to the top face of the walls 44 in order to achieve a smooth transition between the top face and the valve face to ensure sealing contact between the walls and the sensor surface in the closed docking state.

In order to achieve well defined force ranges for the open docking state and the closed docking state respectively, the flow cell unit 32 may comprise one or more force control elements 50a and 50b of elastic material, arranged to stepwise rise the docking force required to further compress the walls 44, at one or both docking states.

Figure 10A:
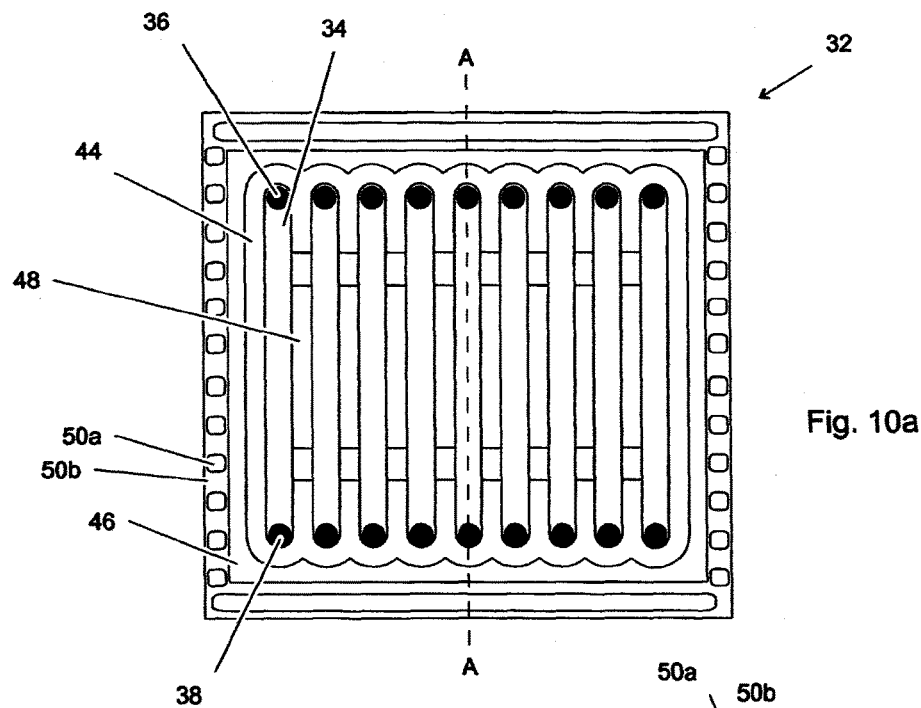
FIGS. 10a to 10d show a flow cell unit according to one embodiment and the basic control of docking force.
Figure 10B:
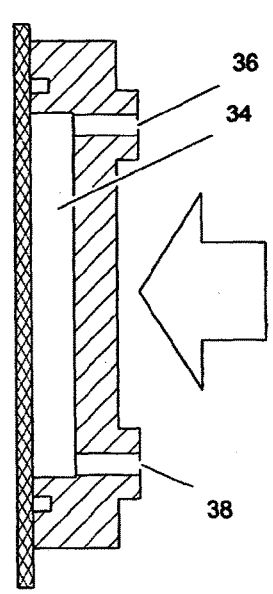
Figure 10C:
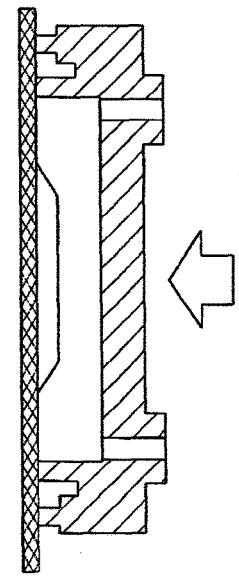
Figure 10D:
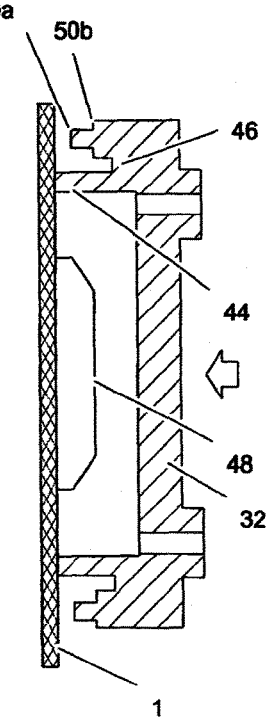

FIG. 10a is a top view of a flow cell unit 32 with 9 adjacent elongated flow channels 34a-i defined by walls 44. And FIGS. 10b-d shows the flow cell unit 32 of FIG. 10a in cross section along in three different docking force states. According to one embodiment schematically disclosed in FIG. 10d, the walls 44 protrudes slightly further from the top surface 46 than the force control elements 50a. Thereby the walls 44 are compressed slightly before the force control elements 50a abuts the sensor surface 1, as is illustrated in FIG. 10c, whereby the force needed to compress the walls 44 of the flow cell unit 32 increases in a stepwise manner creating a well-defined and sufficiently broad force range for the open docking state. Similarly, after applying further force, compressing both the walls 44 and the force control elements 50a further until force control elements 50b is reached and the force needed to compress the walls 44 further increases a second time in a stepwise manner, thus creating a well-defined and sufficiently broad force range for the closed docking state. It should be noted that one of or both of the force control elements 50a and 50b may be omitted in case the docking force may be controlled in a sufficiently precise manner. The dimensions of the walls 44, flow channels 34, valve sections 48, force control elements 50a and 50b etc. need to be adapted to the specific flow cell dimensions and requirements, which will be apparent to the skilled person.

Figure 11A:
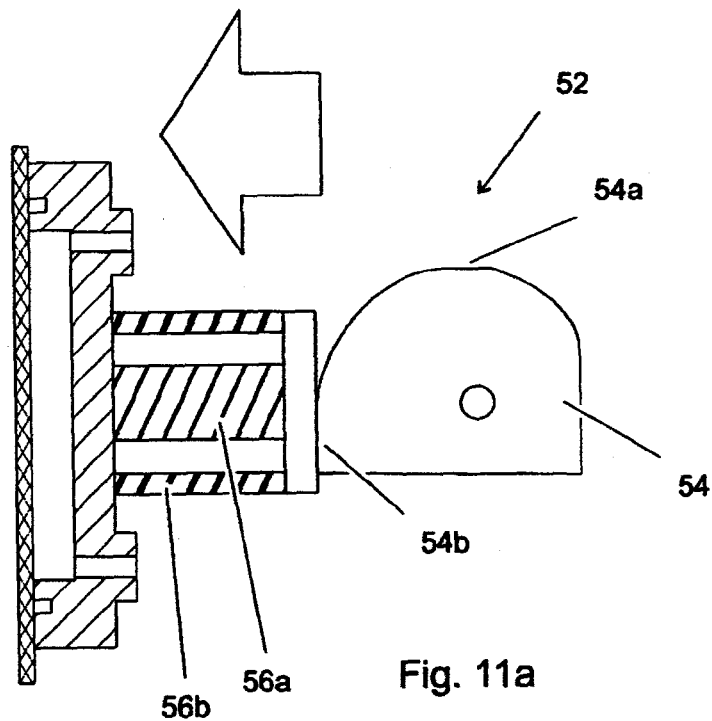
FIGS. 11a and 11b show a docking unit according to one embodiment.
Figure 11B:
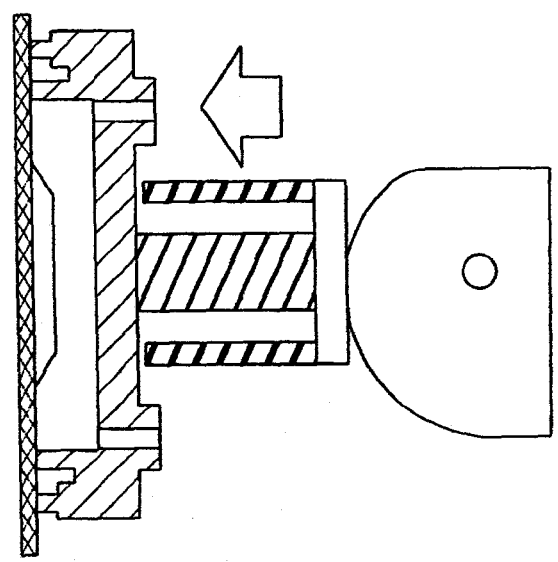

FIGS. 11a and 11b shows one schematic example of a docking unit 52 arranged to control docking force between flow cell and the sensor surface 1 to an open docking state and a closed docking state respectively. The disclosed docking unit 52 is a mechanical arrangement based on a cam type actuator 54 with predefined docking force positions 54a and 54b for the open and closed state respectively. In order to provide predefined docking force in the two docking states, the docking unit 52 comprises a force control arrangement, e.g. comprised of two parallel spring elements 56a and 56b of different length. In this way only one spring element 56a is engaged in the open docking state shown in FIG. 11b whereby the applied force is controlled by the characteristic of spring element 56a. Whereas in the closed docking state, both spring elements 56a and 56b are engaged and the applied force is controlled by the combined characteristics of the two spring elements 56a and 56b.

According to an alternative embodiment, there is provided a docking force sensor and the docking unit is arranged to apply a predefined force based on feedback from the force sensor. In a SPR biosensor system the docking force sensor may be replaced by SPR based sensing of the docking force states, as it will be possible to register a change in the SPR response when the valve face 48 abuts the sensor surface 1.

As can be appreciated by a skilled person, the desired docking force level for the different open and closed states respectively, may be achieved by precise and repeatable positioning of the docking unit 52 without any registration or specific control of the docking force.

Figure 12A:
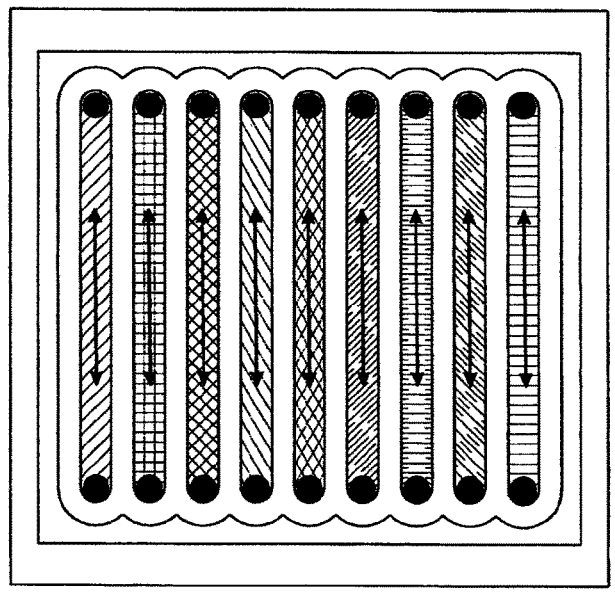
FIGS. 12a and 12b show the flow cell unit of FIGS. 10a-d in closed and open docking force state, respectively.
Figure 12B:
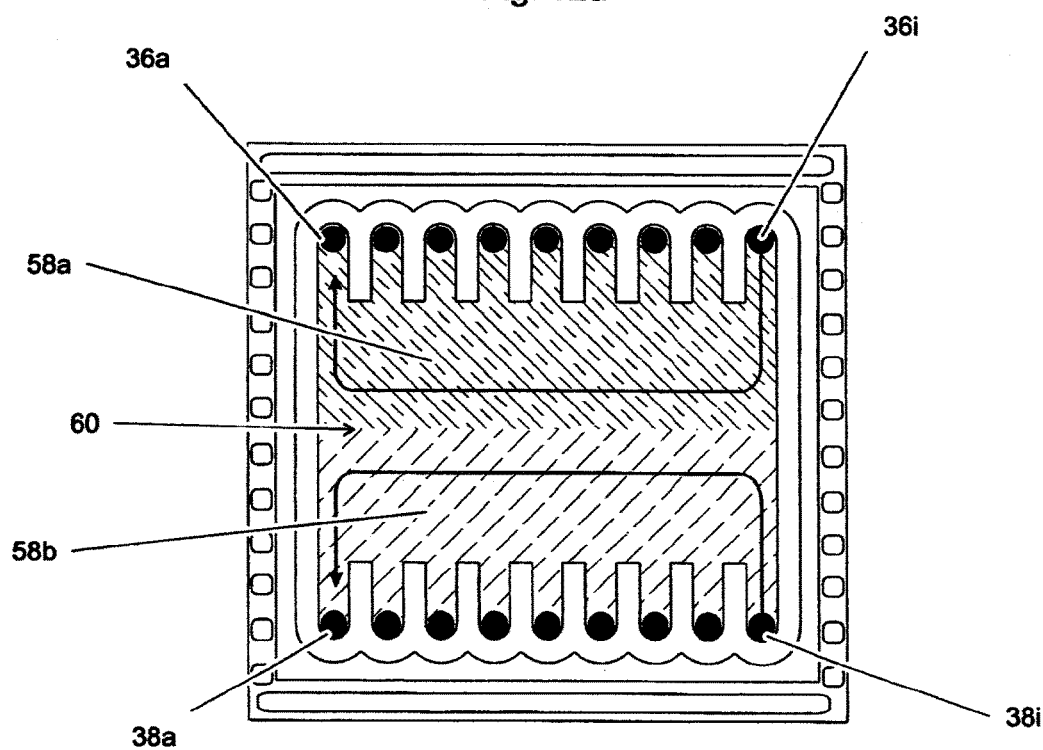

FIG. 12*a* shows the flow cell unit 32 of FIG. 10*a* in the closed docking force state, whereby 9 separate flow channels 34*a-i* are formed, and 9 different sample solutions may e.g. be introduced in parallel. Similarly, FIG. 12*b* shows the flow cell unit 32 in the open docking force state whereby there is provided a flow path transverse to the elongated flow channels. As is shown in the disclosed example, two different sample fluids may be introduced through ports 36*i* and 38*i* at one end in the transverse direction and extracted at ports 36*a* and 38*a* the other end, thereby creating a transverse laminar flow with a well-defined interface 60. In this way two different transverse sections 58*a* and 58*b* of the sensor surface can be addressed independently by suitable reagents to create two different detection surface states, e.g. during immobilization and/or detection steps in a biosensor system.

Figure 13A:
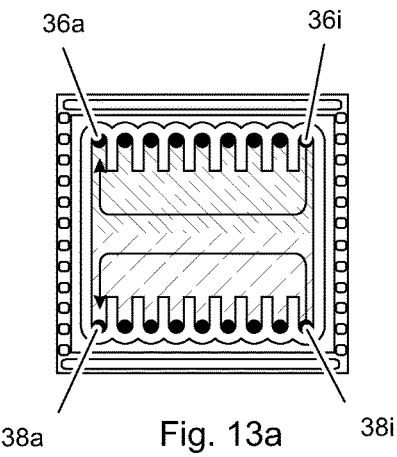
FIGS. 13a to 13e show an example of an immobilization and detection process using the flow cell unit according FIGS. 10a-d.
Figure 13B:
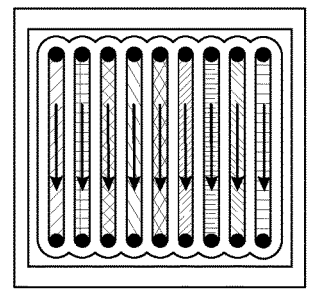
Figure 13C:
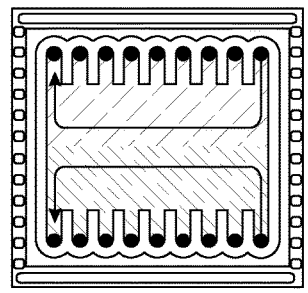
Figure 13D:
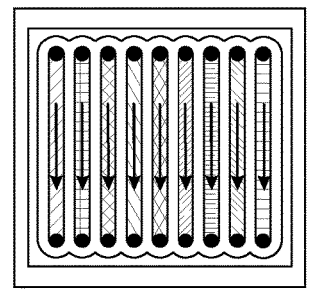
Figure 13E:
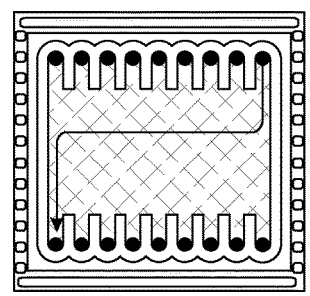
Figure 13F:
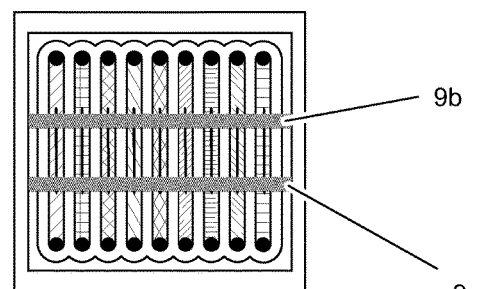

FIGS. 13*a-f* shows one possible series of process steps wherein the flow cell arrangement according to the present invention is utilized to immobilize ligands for detection using a two-line SPR biosensor, comprising the following steps:

1. Activation of a first section 58*a* by flowing activation fluid from port 36*i* to port 36*a*, while flowing a protecting fluid e.g. buffer from port 38*i* to port 38*a*. (FIG. 13*a*)
2. Flowing ligand solutions along flow channels 34*a-i* whereby ligands get immobilized in the intersecting region of each channel and the first section 58*a* forming detection spots along the SPR detection line 9*b*. (FIG. 13*b*)
3. Deactivation of the first section 58*a* by flowing deactivation fluid from port 36*i* to port 36*a*, while flowing a protecting fluid e.g. buffer from port 38*i* to port 38*a*. (FIG. 13*c*)
4. Optionally repeating steps a to c for the second section 58*b* to correspondingly immobilize ligands at intersecting regions of said section forming detection spots along the SPR detection line 9*a*. (FIGS. 13*a-c*), Alternatively, the detection spots in the second section 58*b* are left blank as reference spots.
5. Flowing analyte solutions along flow channels 34*a-i* while registering interaction responses for the detection spots 13 along the SPR detection lines 9*a* and 9*b* (FIG. 13*d*)
6. Regenerating the immobilized ligands at all detection spots 13 simultaneously by flowing regeneration fluid from ports 36*i* and 38*i* to ports 36*a* and 38*a*. (FIG. 13*e*)

Figure 14A:
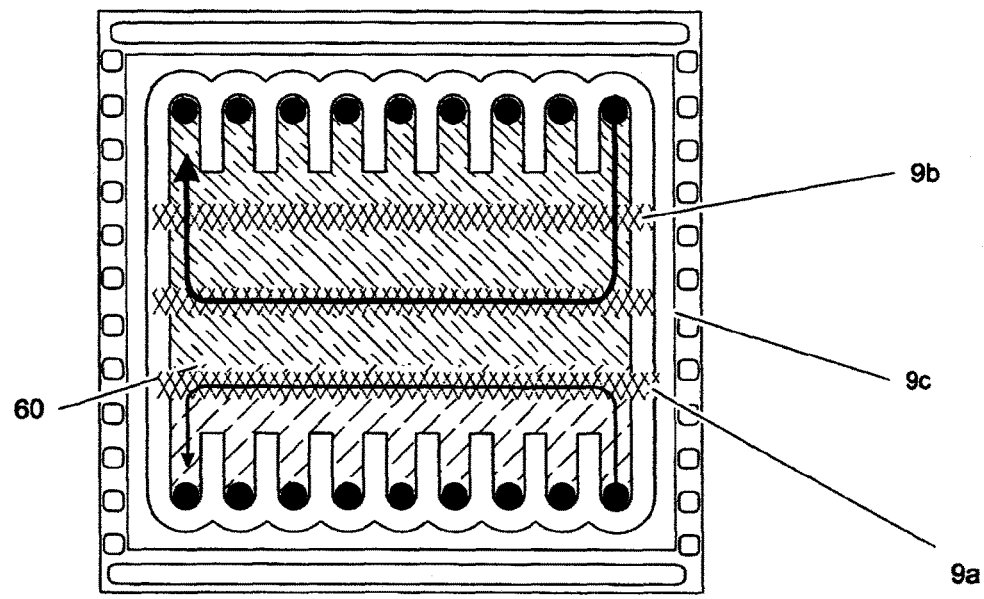
FIGS. 14a and 14b show the flow cell unit of FIGS. 10a-d in open docking force state, wherein a fluid interface is shifted using hydrodynamic control.
Figure 14B:
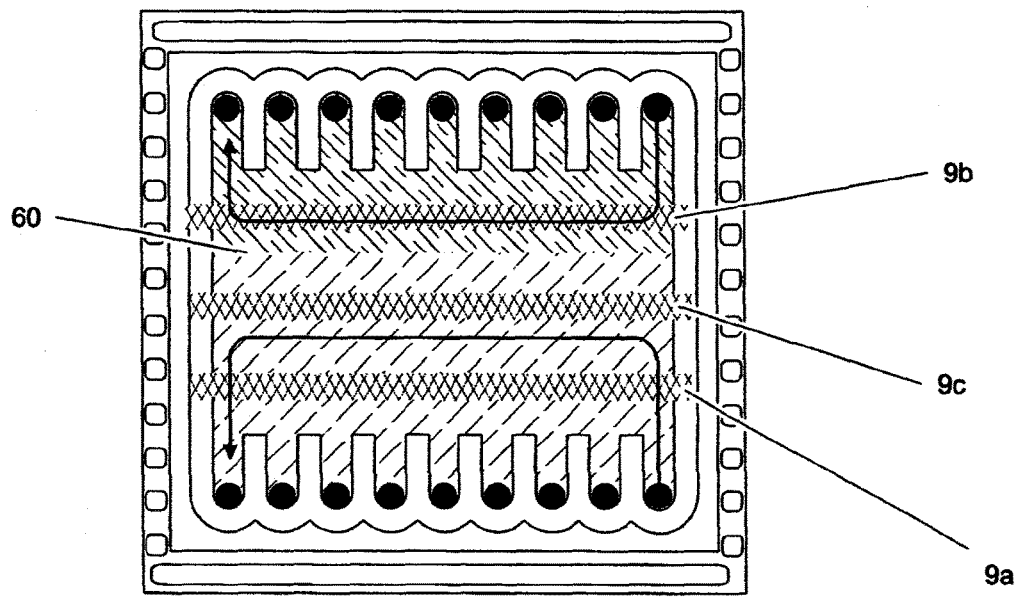
Figure 15A:
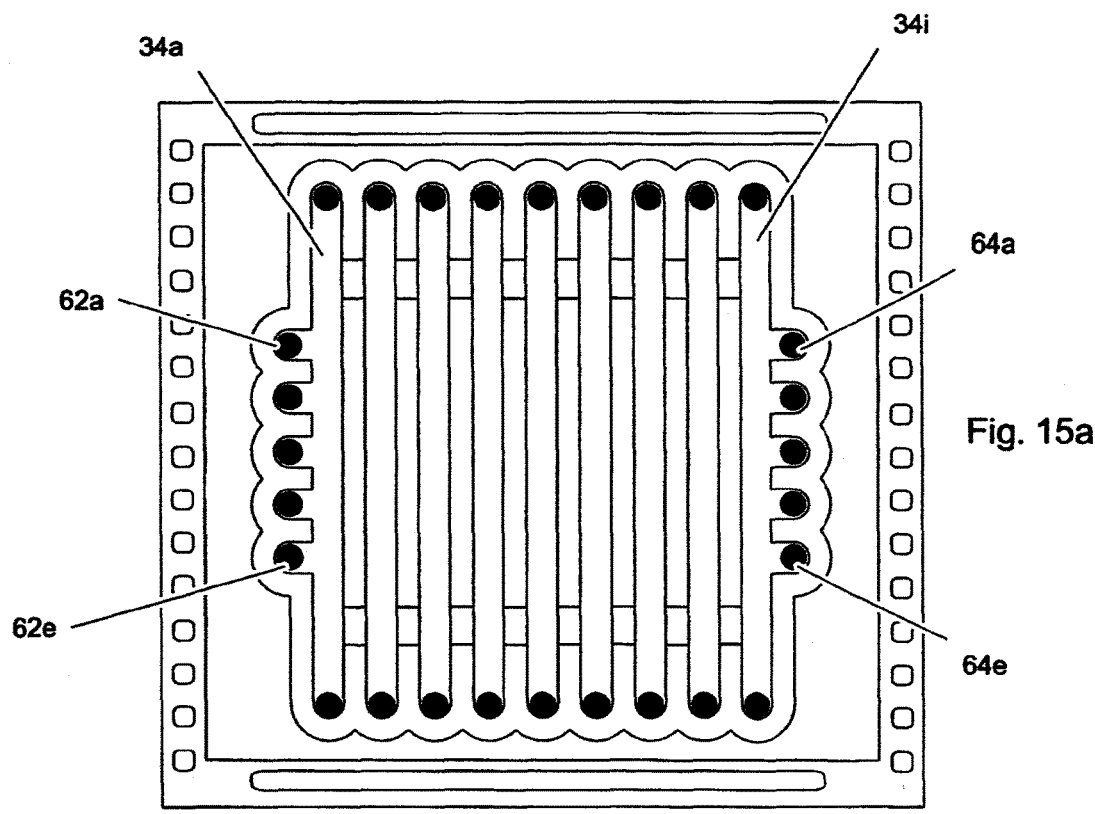
FIGS. 15a to 15d show a flow cell unit according to an alternative embodiment.
Figure 15B:
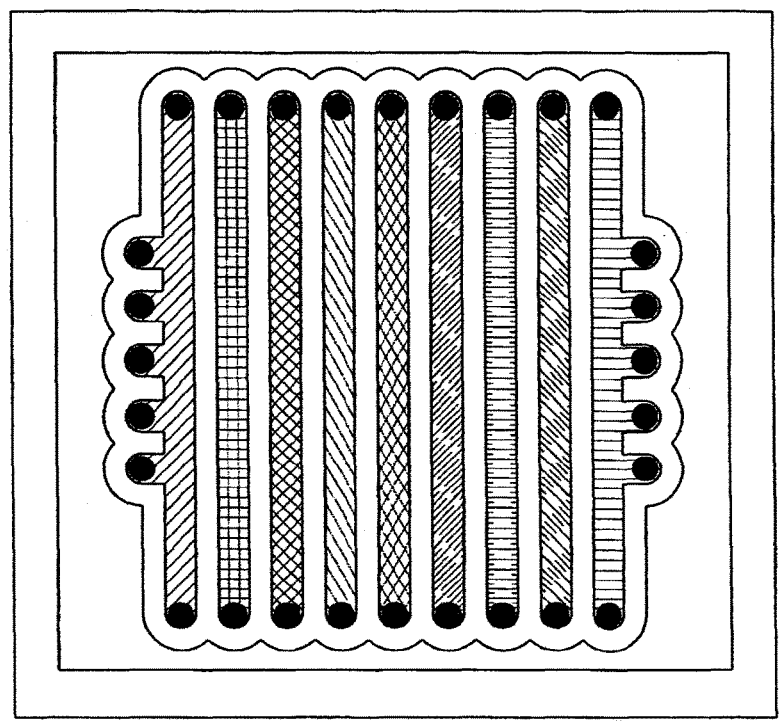
Figure 15C:
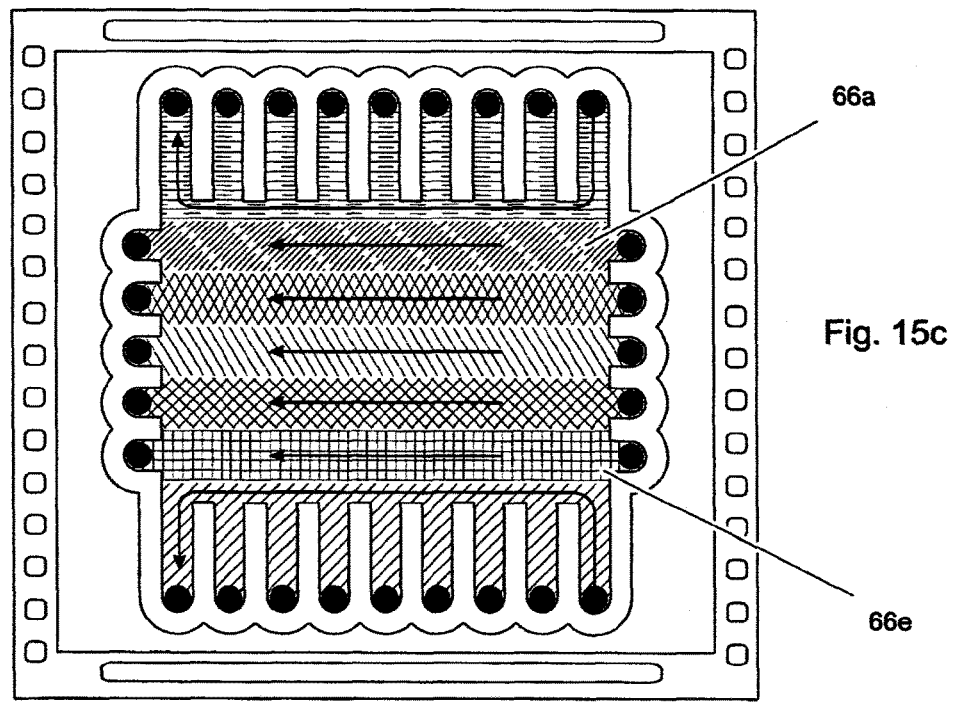
Figure 15D:
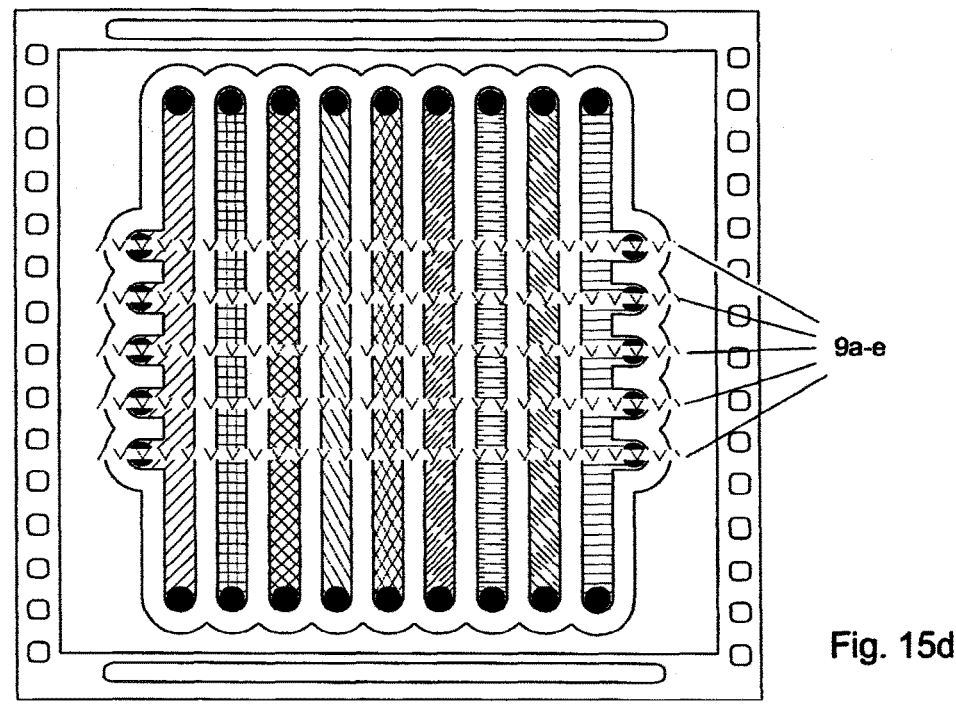

FIGS. 14*a* and 14*b* show one embodiment, where the interface position 60 of the transverse flowpath is shifted by controlling the relative flow rates of the two fluids, e.g. to provide hydrodynamic addressing of one or more additional transverse detection lines 9*c*. Various methods of achieving hydrodynamic positioning of such an interface are e.g. disclosed in U.S. Pat. No. 7,811,515, U.S. Pat. No. 7,219,528, U.S. Pat. No. 7,015,043 and WO2003102580, which all are incorporated by reference.

FIGS. 15*a* to 15*d* shows an alternative embodiment comprising 5 transversely arranged inlet-outlet pairs 62-64*a-e* arranged to provide dedicated transverse laminar flow channels 66*a-e* along the transverse flow path during the open docking force state, thus avoiding the need for hydrodynamic positioning of the interface 60 to address additional detection areas on the sensor surface 1. In the disclosed embodiment, the ports of the inlet-outlet pairs 62-64*a-e* are arranged in the outer flow channels 34*a* and 34*i* respectively and said outer flow channels are shown to be used as ordinary flow channels during e.g. immobilization and/or detection, but in an alternative embodiment (not shown), the inlet-outlet pairs 62-64*a-e* may be arranged in separate outer compartments not used as flow channels and which are opened and closed by a corresponding valve section 48. As is disclosed in FIG. 15*c*, the inlet-outlet pairs 62-64*a-e* are arranged to provide laminar flow channels 66*a-e*, and in order to avoid distortion at the outer laminar flow channels 66*a* and 66*e* respectively, a laminar flow may also be established between the outermost first and second fluid ports 36, 38 respectively. By this arrangement a large number of detection spots may be provided in an array where the fluid channels 34*a-i* crosses the laminar flow channels 66*a-e*. i.e. 45 independent detection spots.

Figure 16A:
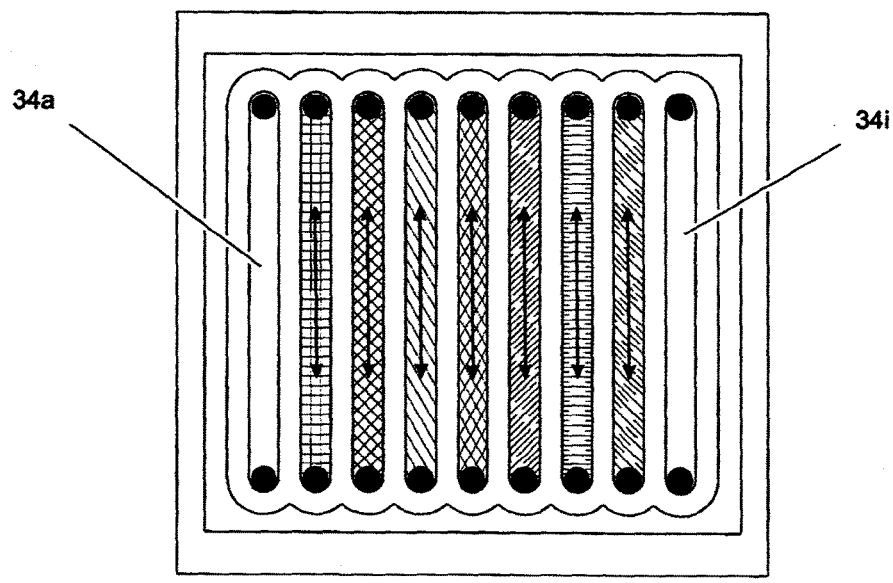
FIGS. 16a and 16b show a flow cell unit according to an alternative embodiment.
Figure 16B:
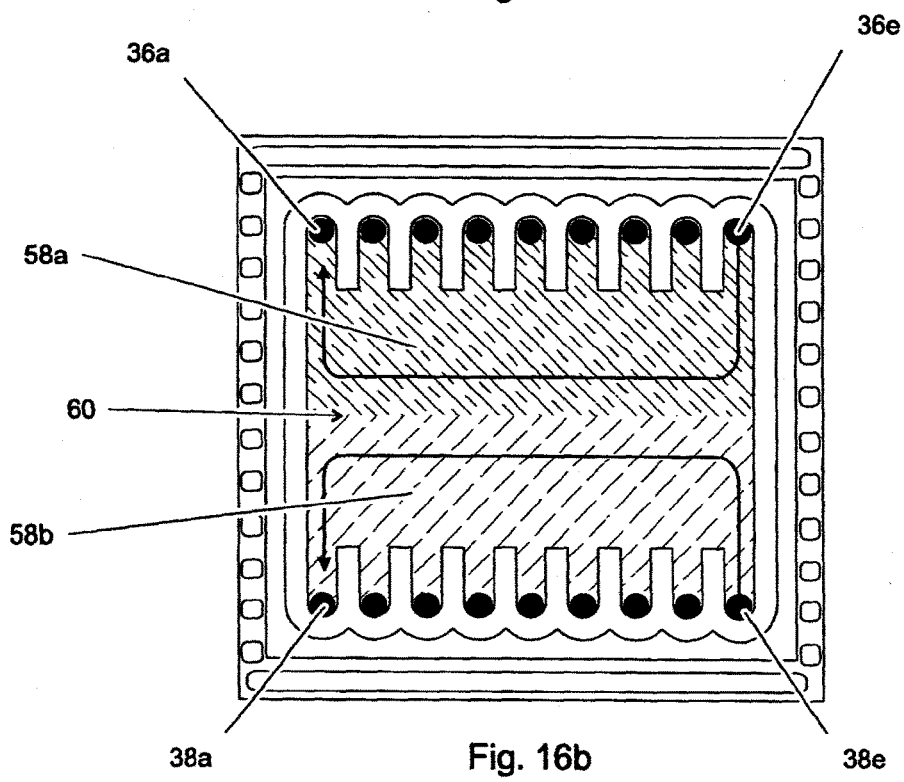

FIGS. 16*a* and 16*b* shows an alternative use of the flow cell arrangement as disclosed in FIGS. 12*a* to 14*b*, wherein the outermost channels 34*a* and 34*i* and the associated ports 36*a*, 36*i*, 38*a* and 38*i* are dedicated for transverse flow only. By this restriction, liquid handling of reagents in the form of activation, deactivation and regeneration fluids is separated from the liquid handling of ligand and analyte sample solutions. By this separation time consuming washing steps etc can be eliminated for many types of interaction experiments. In an alternative embodiment, the ports 36*a*, 36*i*, 38*a* and 38*i* dedicated for transverse flow only are arranged in positions optimized for laminar transverse flow in the flow cell in a similar way as the inlet outlet pairs 62*a*-64*a* in FIG. 15*a*.

What is claimed is:

1. A flow cell unit to be docked against a flat lid surface to form a closed flow cell arrangement, the flow cell unit comprising:
   a top surface with protruding walls of elastic material defining three or more adjacent elongated flow channels, wherein the protruding walls separating adjacent flow channels comprise a valve section of reduced height that allows for selective opening and closing of a transverse flow path that is transverse to the elongated flow channels;
   wherein each flow channel comprises a first fluid port and a second fluid port;
   wherein the selective opening and closing of the transverse flow path is controllable by adjusting a docking force between the protruding walls and the lid surface; and
   wherein the valve section in the protruding walls comprises a flat valve face and inclined segments extending from the valve face to a top surface of the protruding walls, and the docking force is configured to position the protruding walls to be in a first position when the valve face is not in sealing contact with the lid surface, thereby providing an open docking state with the transverse flow path open; and a second position when the valve face abuts the lid surface, thereby providing a closed docking state with the transverse flow path closed.

2. The flow cell unit according to claim 1 further comprising one or more force control elements of elastic material arranged to stepwise rise the docking force required to further compress the walls, at one or both docking states.

3. The flow cell unit according to claim 1 further comprising one or more transversely arranged inlet-outlet pairs arranged to provide transverse laminar flow channels along the transverse flow path.

4. The flow cell unit according to claim 2, wherein the protruding walls protrudes further from the top surface than the force control elements.

5. The flow cell unit according to claim 1, wherein the selective opening and closing of the transverse flow path is controllable by adjusting the docking force between the protruding walls and the lid surface with the docking force provided by a docking unit.

6. The flow cell unit according to claim 5, wherein the docking unit is a mechanical arrangement.

7. The flow cell unit according to claim 6, wherein the docking unit comprises an actuator.

8. The flow cell unit according to claim 6, wherein the docking unit comprises parallel spring elements of different length.

9. The flow cell unit according to claim 5, wherein the docking unit is arranged to apply a predefined force based on sensor feedback.

10. The flow cell unit according to claim 5, wherein the docking force is sensed based on a Surface Plasmon Resonance (SPR) response.

11. The flow cell unit according to claim 10, wherein a change in the SPR response is registered when the valve face abuts the lid surface.

* * * * *